US010342425B1

(12) United States Patent
Rana et al.

(10) Patent No.: US 10,342,425 B1
(45) Date of Patent: Jul. 9, 2019

(54) METHOD AND SYSTEM FOR CONTROLLING ILLUMINATORS

(71) Applicant: Tobii AB, Danderyd (SE)

(72) Inventors: Pravin Rana, Danderyd (SE); Daniel Tornéus, Danderyd (SE); Jonas Andersson, Danderyd (SE)

(73) Assignee: Tobii AB, Danderyd (SE)

( * ) Notice: Subject to any disclaimer, the term of this patent is extended or adjusted under 35 U.S.C. 154(b) by 0 days.

(21) Appl. No.: 15/938,746

(22) Filed: Mar. 28, 2018

(51) Int. Cl.
| | | |
|---|---|---|
| *A61B 3/11* | (2006.01) | |
| *A61B 3/113* | (2006.01) | |
| *G06F 3/01* | (2006.01) | |
| *G02B 27/01* | (2006.01) | |
| *G06K 9/00* | (2006.01) | |

(52) U.S. Cl.
CPC ............ *A61B 3/113* (2013.01); *G02B 27/017* (2013.01); *G06F 3/013* (2013.01); *G06K 9/00604* (2013.01)

(58) Field of Classification Search
CPC ....... A61B 3/113; G02B 27/017; G06F 3/013; G06K 9/00604
See application file for complete search history.

(56) References Cited

U.S. PATENT DOCUMENTS

| 7,572,008 B2 | 8/2009 | Elvesjo et al. |
| 8,866,702 B1 | 10/2014 | Wong et al. |
| 9,041,787 B2 | 5/2015 | Andersson et al. |

FOREIGN PATENT DOCUMENTS

EP 3 079 560 B1 12/2014

*Primary Examiner* — Jack Dinh

(57) ABSTRACT

A method for controlling illuminators in an eye tracking system and a corresponding system are disclosed. The system includes a plurality of illuminators arranged such that each illuminator of the illuminators is located at a respective fixed position in relation to an eye of a user when using the system. The method comprises illuminating the eye of the user by means of the plurality of illuminators, and receiving an image of the eye of the user from an image sensor, the image resulting from the image sensor detecting light from the plurality of illuminators reflected from the eye of the user and reflected from an optic arrangement located between the plurality of illuminators and the eye of the user. The method further comprises determining a pupil position of a representation in the image of a pupil of the eye, and identifying one or more blobs in the image, wherein a blob is a representation in the image of a reflection from the optic arrangement of light from an illuminator of the plurality of illuminators. On a condition that there is at least one blob of the one or more blobs for which one or more predefined criteria are met, the method comprises identifying an illuminator of the plurality of illuminators associated with the at least one blob of the one or more blobs, and switching off the identified illuminator of the plurality illuminators.

18 Claims, 7 Drawing Sheets

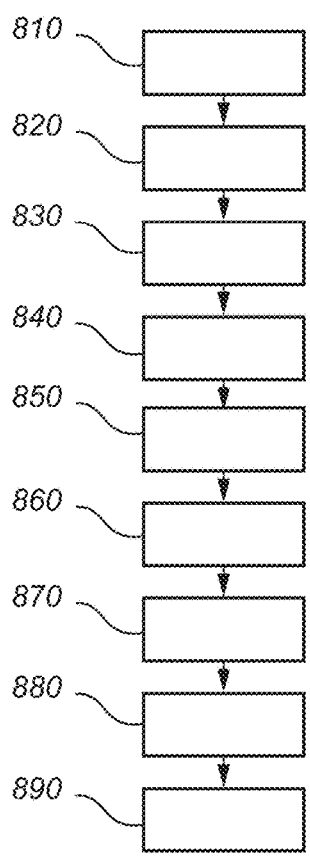
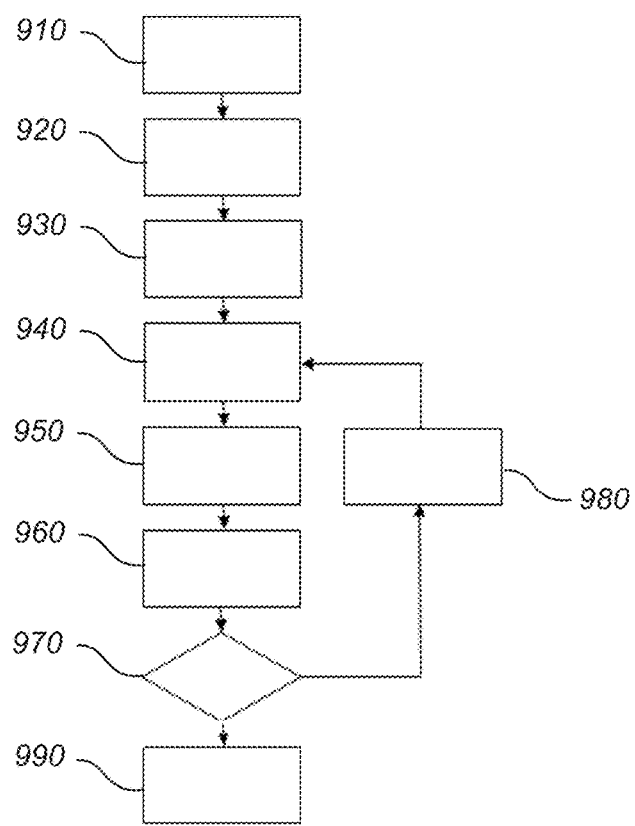
Fig. 8
Fig. 9

METHOD AND SYSTEM FOR CONTROLLING ILLUMINATORS

TECHNICAL FIELD

The present disclosure generally relates to the field of eye tracking. In particular, the present disclosure relates to systems and methods for use in controlling illuminators in an eye tracking system.

BACKGROUND

In eye tracking applications, digital images are retrieved of the eyes of a user and the digital images are analyzed in order to estimate the gaze direction of the user. There are different methods for achieving such an estimation. In some methods ambient light is used when retrieving images of the eyes of the user and in some methods additional light sources (illuminators) are used to illuminate the eyes for retrieving images of the eyes of the user. Generally, the estimation of the gaze is based on identification of the pupils of the eyes of the user, together with identification of glints (corneal reflections) in the eyes of the user. In order to identify a pupil of an eye in an image of the eye, the contrast between a representation of the pupil and a representation of an iris of the eye in the image must be sufficient.

One known method of eye tracking includes the use of infrared light and an image sensor. The infrared light is directed towards the pupil of a user and the reflection of the light is captured by an image sensor. Through analysis of the reflection point, the direction of the user's gaze may be calculated. One such system is described in U.S. Pat. No. 7,572,008 (which is hereby incorporated by reference in its entirety).

Portable or wearable eye tracking devices have also been previously described. One such eye tracking system is described in U.S. Pat. No. 9,041,787 (which is hereby incorporated by reference in its entirety). A wearable eye tracking device is described using illuminators and image sensors for determining gaze direction.

In applications of eye tracking for in portable or wearable eye tracking devices, such as in virtual reality (VR) devices, where head mounted devices are used which include an eye tracking system determining an eye direction and/or gaze direction based on a pupil center and glints from illuminators illuminating a user's eyes, problems can arise for example for a user who is wearing a pair of spectacles under the VR glasses. For example, one or more reflections from an optic arrangement of the pair of spectacles caused by the one or more of the illuminators may result in a situation where the pupil cannot be accurately identified or where no or too few glints can be identified for eye tracking. In such situations it will be difficult or impossible to determine eye direction and/or gaze direction and or eye direction or at least not with desirable reliability.

It would be desirable to provide an eye tracking technology to account for such situations where reflections from glasses worn under VR glasses reduce the accuracy of eye tracking or makes it difficult or impossible to determine eye direction and/or gaze direction for eye tracking.

SUMMARY

An object of the present disclosure is to address at least one of the issues with known systems and methods.

According to a first aspect, there is provided a method of controlling illuminators in an eye tracking system. The system includes a plurality of illuminators arranged such that each illuminator of the illuminators is located at a respective fixed position in relation to an eye of a user when using the system.

In the method the eye of the user is illuminated by means of the plurality of illuminators and an image of the eye of the user is received from an image sensor. The image is the result of the image sensor detecting light from the plurality of illuminators reflected from the eye of the user. In addition to the reflected light from the eye of the user, reflected light from an optic arrangement located between the plurality of illuminators and the eye of the user is also detected by the image sensor.

A pupil position of a representation in the image of a pupil of the eye is then determined and one or more blobs are identified in the image. A blob is a representation in the image of a reflection from the optic arrangement of light from an illuminator of the plurality of illuminators.

On a condition that there is at least one blob of the one or more blobs for which one or more predefined criteria are met, an illuminator of the plurality of illuminators associated with the at least one blob of the one or more blobs is identified and the identified illuminator of the plurality illuminators is switched off.

As indicated above, some factors that may potentially cause difficulty of determination of gaze direction remain in known method and systems based on identification of the pupils of the eyes of the user together with identification of glints (corneal reflections). For example, in a situation where representations of reflections (called blobs herein) from an optic arrangement located between the plurality of illuminators and the eye of the user appear in the image in addition the representation of the reflections from the eye of the user, such blobs may affect the possibility to identify the glints and/or the representation of the pupil in the image such that it will be difficult or impossible to determine eye direction and/or gaze direction or at least not with desirable accuracy. Identifying an illuminator that causes a blob which meets a one or more criteria, and switching of the identified illuminator enables cancelling of blobs in the image which affect the possibility to identify the representation of the pupil in the image and/or the glints.

The system may be a wearable system (head mounted system), such as a virtual reality (VR) system where goggles are used arranged on the head of the user, such that illuminators arranged in the head mounted system will move together with the head of the user and hence the illuminators will be fixed in relation to the eyes of the user when the system is used by the user. It is to be noted that the illuminators are fixed in relation to the eyes of the user provided that the VR device does not move in relation to the head during use.

The image sensor can be any suitable type of imaging sensor.

The eye may for example be illuminated by a plurality of illuminators which may for example be light sources such as light emitting diodes and the light emitted may be visible light or infrared light.

The optic arrangement located between the plurality of illuminators and the eye of the user when the user is using the eye tracking system may be any optic arrangement that converges or diverges light, such as a lens/glass of a pair of spectacles worn by the user in addition to and separate to the eye tracking system.

The determination of the pupil position may be done by means of any suitable method for determination of pupil position.

It is to be noted that illuminators are generally only emitting light during exposure of an image. At other times all illuminators would not emit light, e.g. in order to preserve energy which would be particularly relevant for a battery driven system. Hence, all illuminators will emit light only a portion of the time. Indicating that an illuminator is switched off is intended to mean that the illuminator will not emit light even when an image is being captured.

In order to maintain the brightness after switching off one or more illuminators, the luminance of one or more of the illuminators not switched off the camera's imaging parameters may be controlled to compensate for the reduced luminance due to the switching off of one or more illuminators.

In some embodiments, a respective position of the one or more blobs in the image, a respective distance from the respective position of the one or more blob to the pupil position, and a respective size of the one or more blobs are determined. Furthermore, the one or more predefined criteria are a predefined distance criterion and/or a predefined size criterion. The determined distances and/or sizes are then compared to the predefined distance criterion and/or the predetermined size criterion, respectively. On a condition that the determined distance of at least one blob of the one or more blobs meets the predefined distance criterion and/or the determined size of the at least one blob of the one or more blobs meets the predefined size criterion, an illuminator of the plurality of illuminators associated with the at least one blob of the one or more blobs is identified, and the identified illuminator of the plurality illuminators is switched off.

Identifying an illuminator that causes a blob which meets a distance criterion and/or a size criterion and switching of the identified illuminator enables cancelling of blobs which affect the possibility to identify glints and/or a representation of the pupil in an image.

The distance criterion may for example be that the determined distance is below a predefined distance. For example, the predefined distance may be determined as a distance from the pupil center below which a blob may affect the possibility to identify the representation of the pupil in and/or the glints the image and above which a blob may not affect the possibility to identify the representation of the pupil in the image and/or the glints.

The size criterion may for example be that the determined size is above a predefined size. For example, the predefined size may be determined as a size above which a blob may affect the possibility to identify the representation of the pupil in the image and/or the glints and below which a blob may not affect the possibility to identify the representation of the pupil in the image and/or the glints.

In some embodiments, the pupil position is determined as the position of the center of the representation of the pupil in the image.

In some embodiments the position of the blob is determined as the position the center of mass of the blob. Generally, the shape of the blob is not determined. However, by determining the position of the blob by means of its center of mass will at least to some extent encompass the shape in relation to the extent to which the blob will affect the possibility to identify the representation of the pupil in the image and/or the glints.

In some embodiments, the identification of an illuminator of the plurality of illuminators is based on first dividing the image into two or more regions. A region of the two or more regions in which the at least one blob of the one or more blobs is located is identified and a subset of illuminators of the plurality of illuminators, wherein the subset of illuminator is associated with the identified region.

An illuminator of the identified subset of illuminators is then switched off and a further image of the eye is received from the image sensor. The further image is the result of the image sensor detecting light from the plurality of illuminators, except the illuminator being switched off, reflected from the eye of the user and reflected from the optic arrangement located between the plurality of illuminators and the eye of the user.

If the at least one blob of the one or more blobs is still in the further image, the illuminator switched off did not cause the at least one blob of the one or more blobs. Hence, the steps of switching off an illuminator and receiving a further image is repeated for a different illuminator of the subset of illuminators until the at least one blob of the one or more blobs is not in an image resulting from the image sensor detecting light from the plurality of illuminators, except the illuminator currently being switched off, reflected from the eye of the user and reflected from the optic arrangement located between the plurality of illuminators and the eye of the user.

By dividing the image into at least two regions, the number of illuminators that need to be switched off to determine if that illuminator is causing a blob that meets the one or more predefined criteria, such as the predefined distance criterion and/or the predefined size criterion, is reduced. This enables a reduction of the processing time to identify the illuminator associated with the blob that meets the predetermined distance criterion and/or the predetermined size criterion.

A subset of illuminators being associated with a region of the image may be identified based on the positions of each illuminator of the subset of illuminators. For example, if the image is divided into two regions by a horizontal line through the center of the image this will correspond to a horizontal line through the center of the image sensor. The subset of illuminators including all illuminators arranged above the horizontal line through the center of the image sensor is associated with the region of the image above the horizontal line through the center of the image (corresponding to the horizontal line through the center of the image sensor).

Division of the image in more than two regions, e.g. four regions using one horizontal line through the center of the image and one vertical line through the center of the image will reduce the number of illuminators that will be switched off to determine if that illuminator is causing a blob which meets the predetermined distance criterion and/or the predetermined size criterion. However, depending on how the subset of illuminators associated with a region is identified, it is not necessarily an illuminator of that identified subset of illuminator that is causing a blob in that region which meets the one or more predefined criteria, such as the predefined distance criterion and/or the predefined size criterion. Hence, there may be a tradeoff between processing time and the number of times the illuminator that should be switched off is identified when selecting the number of regions.

In some embodiments, the one or more blobs are further identified in a region of interest (ROI) of the image, the region of interest being a portion of the image including the representation in the image of the pupil.

The region of interest is defined such that blobs outside the region of interest does not affect the possibility to identify the glints and/or the representation of the pupil in the image, whereas blobs inside the region of interest may affect the possibility to identify the glints and/or the representation of the pupil in the image. The region of interest may have any suitable shape, such as rectangle, square, circle, ellipse, etc.

Any blobs outside the region of interest are optionally not identified or at least not processed further. By limiting the one or more blobs identified to any blobs in the region of interest, a reduction of the amount of processing required is enabled. At the same time, not processing blobs outside the region of interest will not, or at least only to a low degree, affect the possibility to identify the representation of the pupil and/or the glints in the image depending on the definition of the region of interest.

In some embodiments, data are recorded on a condition that a blob an illuminator is switched off for a pupil position. For example, data that may be recorded is the pupil position, an identification of the illuminator of the plurality illuminators associated with the at least one blob of the one or more blobs, and, an association between the pupil position and the identification of the illuminator.

The data recorded in relation to a pupil position can be used for control of illuminators in relation to cancelling blobs in images captured for other pupil positions or images for the same pupil position captured at a later instance in time.

In some embodiments, further data are recorded on a condition that an illuminator is switched off for a pupil position. For example, further data that may be recorded are the position of the at least one blob of the one or more blobs and the size of the at least one blob of the one or more blobs.

In some embodiments where the pupil position, an identification of the illuminator of the plurality illuminators associated with the at least one blob of the one or more blobs, and an association between the pupil position and the identification of the illuminator, and possibly the position and the size of the at least one blob of the one or more blobs have been recorded, the recorded data may be used for further images received after the pupil has moved from the pupil position in relation to which the data was recorded and then moved back to the pupil position in relation to which the data was recorded.

In such embodiments, the eye of the user is illuminated by means of the plurality of illuminators and a further image of the eye is received from the image sensor, the further image resulting from the image sensor detecting light from the plurality of illuminators reflected from the eye of the user and reflected from the optic arrangement located between the plurality of illuminators and the eye of the user. A further pupil position of a representation in the further image of a pupil of the eye is determined and for a case where it is determined that the further pupil position is equal to the pupil position as recorded, the recorded data are used to determine an illuminator to switch off. More specifically, the recorded data include an association between the pupil position and the identification of the illuminator associated with the at least one blob of the one or more blobs, i.e. a blob that meets the predefined distance criterion and/or the predefined size criterion in relation to the pupil position.

Hence, the recorded data may be used to identify the illuminator to be switched off without the need for any image processing in relation to identifying blobs, position and size of blobs and distance to a pupil position in an image.

In some embodiments where the pupil position, an identification of the illuminator of the plurality illuminators associated with the at least one blob of the one or more blobs, an association between the pupil position and the identification of the illuminator, and the position and the size of the at least one blob of the one or more blobs have been recorded, the recorded data may be used for further images received after the pupil has moved from a pupil position in relation to which an illuminator is switched off and data was recorded.

After the pupil has moved, the eye of the user is illuminated by means of the plurality of illuminators, except the illuminator as identified by the identification as recorded. A further image of the eye is received from the image sensor, the further image resulting from the image sensor detecting light from the plurality of illuminators, except the illuminator as identified by the identification as recorded, reflected from the eye of the user and reflected from the optic arrangement located between the plurality of illuminators and the eye of the user.

A further pupil position of a representation in further the image of a pupil of the eye is determined, and since the pupil has moved, it is determining that the further pupil position is different from the pupil position as recorded.

The recorded data are used in determining a further distance from the position of the at least one blob as recorded, i.e. a blob that meets the predefined distance criterion and optionally the predefined size criterion in relation to the pupil position before the pupil had moved, to the further pupil position. On a condition that the determined further distance meets the predefined distance criterion maintaining the illuminator identified by the identification as recorded switched off.

In embodiments where data are recorded such as the pupil position, an identification of the illuminator of the plurality illuminators associated with the at least one blob of the one or more blobs, an association between the pupil position and the identification of the illuminator, and the position and the size of the at least one blob of the one or more blobs have been recorded, the recording may be performed continuously for each new pupil position for which no data have been recorded. For pupil positions for which data have been recorded, the recorded data may be used to switch of an illuminator identified by the recorded data, i.e. switching of an illuminator in order to enable removal of a blob in the image may be done instantly as soon as a particular pupil position has been determined.

Hence, the recorded data may be used to identify that a blob for which the one or more predefined criteria, such as a predefined distance criterion and/or a predefined size criterion, are met for a first pupil position would be a blob for which the one or more predefined criteria are met also for a second pupil position without the need for any image processing in relation to identifying blobs, position and size of blobs and distance to a pupil position in an image in relation to the second pupil position. The illuminator causing the blob for which the one or more predefined criteria are met for the first pupil position can remain switched off also directly for capturing images for the second pupil position without the need for first capturing an image for the second pupil position with the illuminator causing the blob for which the one or more predefined criteria are met for the first pupil position switched on.

In some embodiments, a size threshold for identification of a blob is introduced for separating identification of a blob from identification of a glint in the image. For example, a blob can be defined as a representation of a reflection in the image having a size larger than a blob threshold size. Any representation of a reflection in the image larger than the threshold size is identified as a blob. Representation of a reflection in the image smaller than the threshold size is not identified as a blob. Such a reflection in the image smaller than the threshold size may be identified as a glint.

As a blob (representations of reflections from an optic arrangement, such as a lens/glass of a pair of spectacles worn by the user), is generally larger in size than a glint (representation of a corneal reflection), a blob may be defined as a continuous representation of a bright spot in the image which is larger than a predefined number of pixels, where the predetermined number of pixels is preferably set such that it is larger than the number of pixel of glints and smaller than the number of pixels of blobs.

According to a second aspect, there is provided an eye tracking system comprising a plurality of illuminators for illuminating an eye of a user, the plurality of illuminators being arranged at fixed positions in relation to an eye of a user when using the device, and a receiver for receiving an image of the eye of the user from an image sensor, the image resulting from the image sensor detecting light from the plurality of illuminators reflected from the eye of the user and reflected from an optic arrangement located between the plurality of illuminators and the eye of the user.

The system further comprises processing circuitry. The processing circuitry may include a processor (e.g., general purpose processor, specialty purpose processor, microprocessor, programmable logic device, etc.) and/or memory (e.g., computer memory such as random access memory, read only memory, etc.). The processing circuitry is arranged to determine a pupil position of a representation in the image of a pupil of the eye, identifying one or more blob in the image, wherein a blob is a representation in the image of a reflection from the optic arrangement of light from an illuminator of the plurality of illuminators.

The processing circuitry is further arranged to, on a condition that at least one blob of the one or more blobs meets one or more predefined criteria, identify an illuminator of the plurality of illuminators associated with the at least one blob of the one or more blobs, and switch off the identified illuminator of the plurality illuminators.

In some embodiments, the processing circuitry is further arranged to determine a respective position of the one or more blobs in the image, a respective distance from the respective position of the one or more blob to the pupil position, and a respective size of the one or more blobs. the processing circuitry is further arranged to, on a condition that the determined distance of at least one blob of the one or more blobs meets a predefined distance criterion and/or the determined size of the at least one blob of the one or more blobs meets a predefined size criterion, identify an illuminator of the plurality of illuminators associated with the at least one blob of the one or more blobs, and switch off the identified illuminator of the plurality illuminators.

Embodiments of the eye tracking system according to the second aspect may for example include features corresponding to the features of any of the embodiments of the method according to the first aspect.

According to a third aspect, an eye tracking system comprising circuitry configured to perform any one of the method of the first aspect and the embodiments of the first aspect.

Embodiments of the eye tracking system according to the second aspect may for example include features corresponding to the features of any of the embodiments of the method according to the first aspect.

According to a fourth aspect, there is provided one or more computer-readable storage media storing computer-executable instructions that, when executed by an eye tracking system, cause the eye tracking system to perform a method according to the first aspect.

Embodiments of the one or more computer-readable storage media according to the fourth aspect may for example include features corresponding to the features of any of the embodiments of the method according to the first aspect.

The one or more computer-readable media may for example be one or more non-transitory computer-readable media.

It is noted that embodiments of the invention relate to all possible combinations of features recited in the claims.

BRIEF DESCRIPTION OF THE DRAWINGS

Exemplifying embodiments will be described below with reference to the accompanying drawings:

FIGS. 7-11 are flow charts of methods according to embodiments.

All the figures are schematic and generally only show parts which are necessary in order to elucidate the respective embodiments, whereas other parts may be omitted or merely suggested.

DETAILED DESCRIPTION

Figure 1:
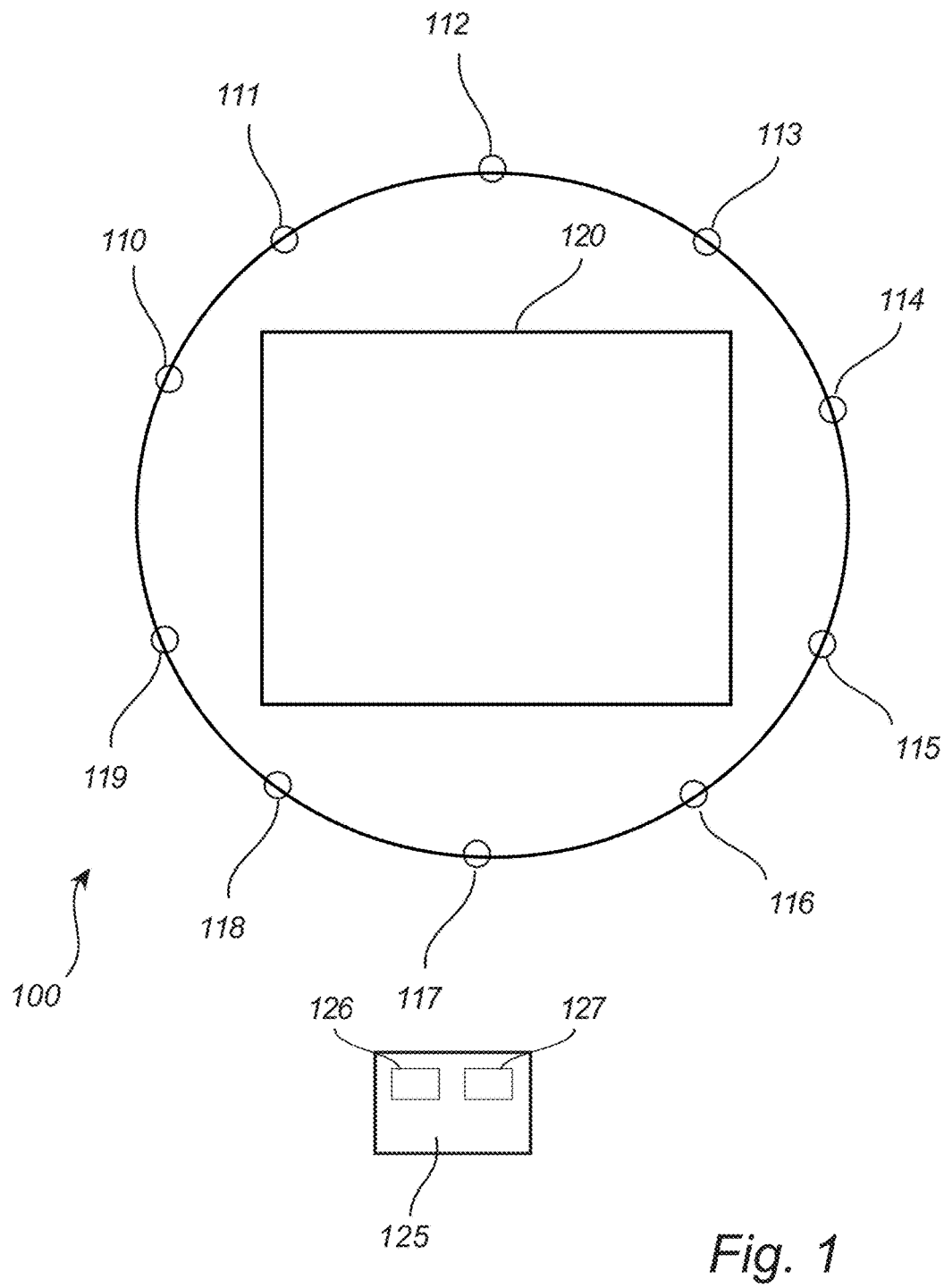
FIG. 1 shows a schematic view of an eye tacking system, in which embodiments may be implemented.

FIG. 1 shows a simplified view of an eye tacking system 100 (which may also be referred to as a gaze tracking system) in a head mounted device in the form of a virtual reality (VR) device or VR glasses. The system 100 comprises illuminators 110-119 for illuminating the eyes of a user, and a light sensor 120 for capturing images of the eyes of the user. The illuminators 110-119 may for example be light emitting diodes emitting light in the infrared frequency band, or in the near infrared frequency band. The light sensor 120 may for example be an image sensor of any type, such as a complementary metal oxide semiconductor (CMOS) image sensor or a charged coupled device (CCD) image sensor. The image sensor may consist of an integrated circuit containing an array of pixel sensors, each pixel containing a photodetector and an active amplifier. The image sensor is capable of converting light into digital signals. In reality, as an example, it could be Infrared image sensor or IR image sensor RGB sensor RGBW sensor RGB or RGBW sensor with IR filter The eye tracking system 100 also comprises circuitry 125, for example including a receiver 126 and processing circuitry 127, for receiving and processing the images captured by the light sensor 120. The circuitry 125 may for example be connected to the light sensor 120 and the illuminators 110-119 via a wired or a wireless connection and be co-located with the light sensor 120 and the illuminators 110-119 or located at a distance, e.g. in a different device. In another example, the circuitry 125 may be provided in one or more stacked layers below the light sensitive surface of the light sensor 120.

It is to be noted that the location of the image sensor 120 in FIG. 1 is only for illustrative purposes. The location of the sensor for one eye in a VR device is generally away from the line of sight for the user in order not to obscure a VR display arranged in the VR device for that eye. This is e.g. enabled by means of so called hot mirrors which reflects a portion of the light and the rest of the light to pass, e.g. infrared light is reflected and visible light is allowed to pass.

Figure 2:
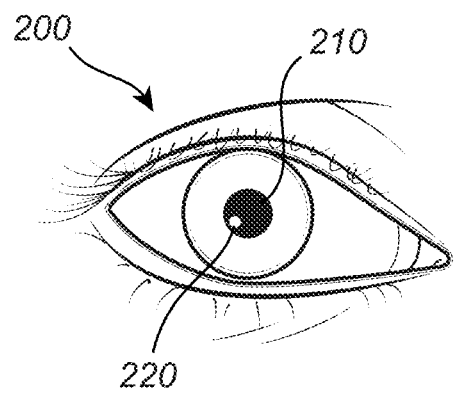
FIG. 2 shows an example image of an eye.

FIG. 2 shows an example of an image of an eye 200, captured by the light sensor 120 of FIG. 1. The circuitry 125 may for example employ image processing (such as digital image processing) for extracting features in the image. The circuitry 125 may for example employ pupil center cornea reflection (PCCR) eye tracking to determine where the eye 200 is looking. In PCCR eye tracking, the position of the center of the pupil 210 and the position of the center of a glint 220 at the eye 200 are estimated in the circuitry 125. The glint 220 is caused by reflection of light from one of the illuminators 110-119. The circuitry 125 calculates where the user's eye is in space using the glint 220 and where the user's eye 200 is pointing using the pupil 210. Since there is typically an offset between the optical center of the eye 200 and the fovea, the circuitry 125 performs calibration of the fovea offset to be able to determine where the user is looking. The gaze directions obtained from the left eye and from the right eye may then be combined to form a combined estimated gaze direction (or viewing direction).

In the eye tracking system described with reference to FIG. 1, the illuminators 110-119 are arranged in an eye tracking module along the periphery of a circle. This arrangement serves only as an example. It will be appreciated that more or less any number of illuminators and light sensors may be employed for eye tracking, and that such illuminators and light sensors may be distributed in different ways relative to displays watched by the user. It will be appreciated that the eye tracking scheme described in the present disclosure may for example be employed for wearable eye tracking (such as in virtual reality (VR) glasses).

Figure 3A:
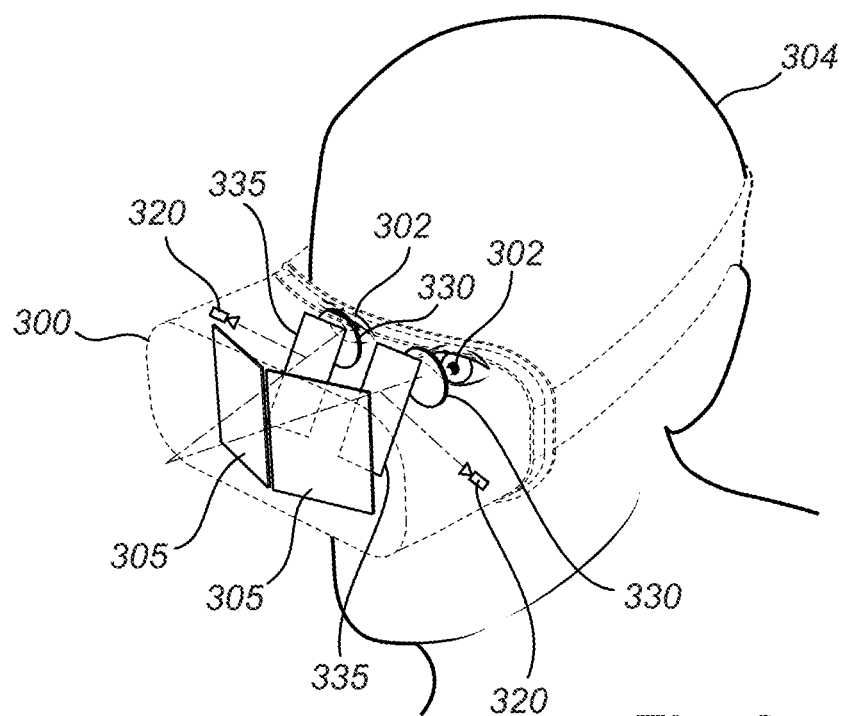
FIG. 3*a* shows a view of selected parts of a head mounted device.
Figure 3B:
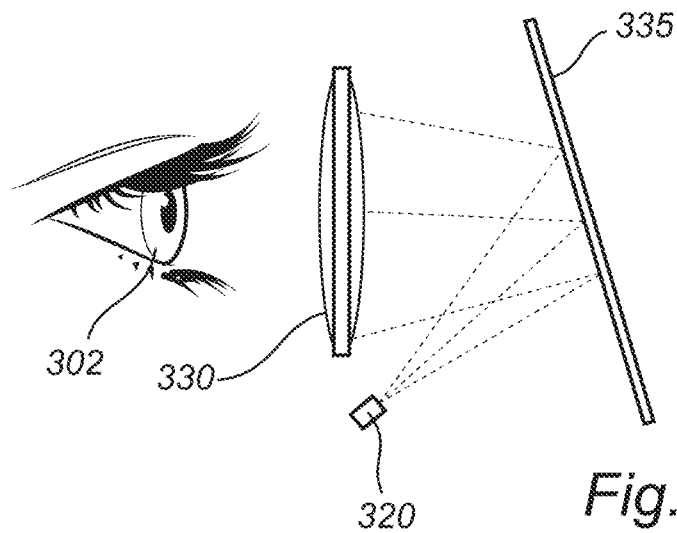
FIG. 3*b* shows a side view of selected parts of a head mounted device.
Figure 3C:
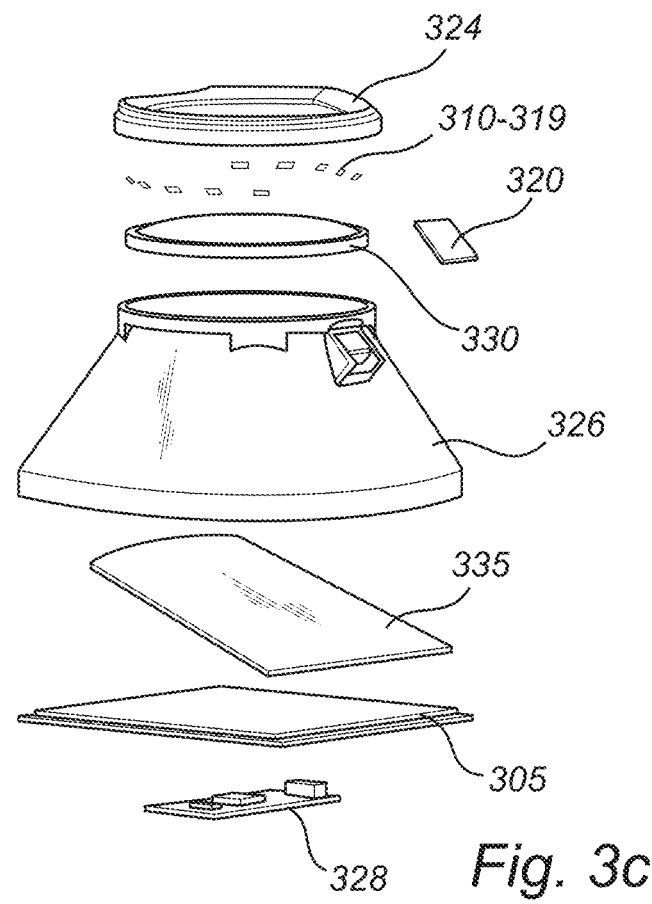
FIG. 3*c* shows an exploded view of selected parts of a head mounted device.

FIGS. 3a-c each show a separate view of selected parts of a head mounted device in the form of a virtual reality (VR) device (VR glasses) 300 including an eye tracking system in which embodiments may be implemented.

FIG. 3a shows a view of selected parts of a head mounted device in the form of the VR glasses 300 including an eye tracking system in which embodiments may be implemented. In addition to the VR glasses 300, eyes 302 and a head 304 of a user are shown. The VR portion of the VR glasses 300 shown comprises two VR displays 305 and two VR lenses 330, one VR display 305 and one VR lens 330 for each eye 302. The VR displays 305 are positioned in front of the eyes 302 and the VR lenses 330 are positioned between the eyes 302 and the VR displays 305. In alternative to two VR displays 305, two regions of a single VR display may be used. The eye tracking portion of the VR glasses 300 comprises two hot mirrors 335 and two cameras 320. In order to capture images of the eyes 302 for use in eye tracking, the hot mirrors 335 are arranged between the VR displays 305 and the VR lenses 330. Furthermore, illuminators (not shown) are arranged on or in the VR glasses 300 such that illumination rays are directed towards the eyes 302. Reflections from the eyes 302 of the illumination rays towards the hot mirrors 335 will reflect towards the cameras 320 in which the illumination rays are detected to produce an image of the eye. For example, the hot mirrors 335 may be of a type such that they will reflect light in the infrared frequency band but be transparent for light in the visible frequency band. The illuminators (not show) used would then produce illumination rays in the infrared frequency band and the cameras 320 will include image sensors able to detect light in the infrared frequency band.

FIG. 3b shows a side view of selected parts of the VR glasses 300. Illumination rays from the illuminators (not shown) towards the eye 302 will reflect back and pass through the VR lens 330 towards the hot mirror 335 and reflect towards the camera 320 in which the illumination rays are detected to produce an image of the eye.

FIG. 3c shows an exploded view of selected parts of the VR glasses 300. Selected parts for one eye are shown including an illuminator cover 324, illuminators in the form of light emitting diodes (LEDs) 310-319, the camera 320 including an image sensor, the VR lens 330, a lens cup or lens tube 326, the hot mirror 335, the VR display 305 and an electronics board 328. FIG. 3c shows an example arrangement of the illuminators in the form of LEDs 310-319, where the LEDs 310-319 are arranged along the periphery of the VR lens 330 to produce a pattern when illuminating the eye 302. The illumination rays from the LEDs 310-319 reflected from the eye and the hot mirror 335 is detected in the camera 320 to produce an image of the eye.

Head mounted devices, such as in VR glasses, can be enhanced by including wearable eye tracking using illuminators and one or more light sensors arranged in the head mounted device for determining eye direction and/or gaze direction based on estimation of a position of a center of the pupil and a position of the center of one or more glints at the eye from the illuminators. A problem that can arise in such devices is that when the user wears spectacles (glasses) under the VR glasses, light from the illuminators can be reflected by the glasses of the spectacles onto the image sensor. Areas of in an image of the eye used for eye tracking corresponding to such reflections are called blobs herein. Such blobs may affect the possibility to identify a representation of the pupil in the image and/or glints such that it will be difficult or impossible to determine eye direction and/or gaze direction or at least not with desirable accuracy.

However, as each blob generally is caused by one illuminator, this illuminator may be identified and switched off. Hence, a new image may be captured by the image sensor in which the blob is no longer present.

Figure 4:
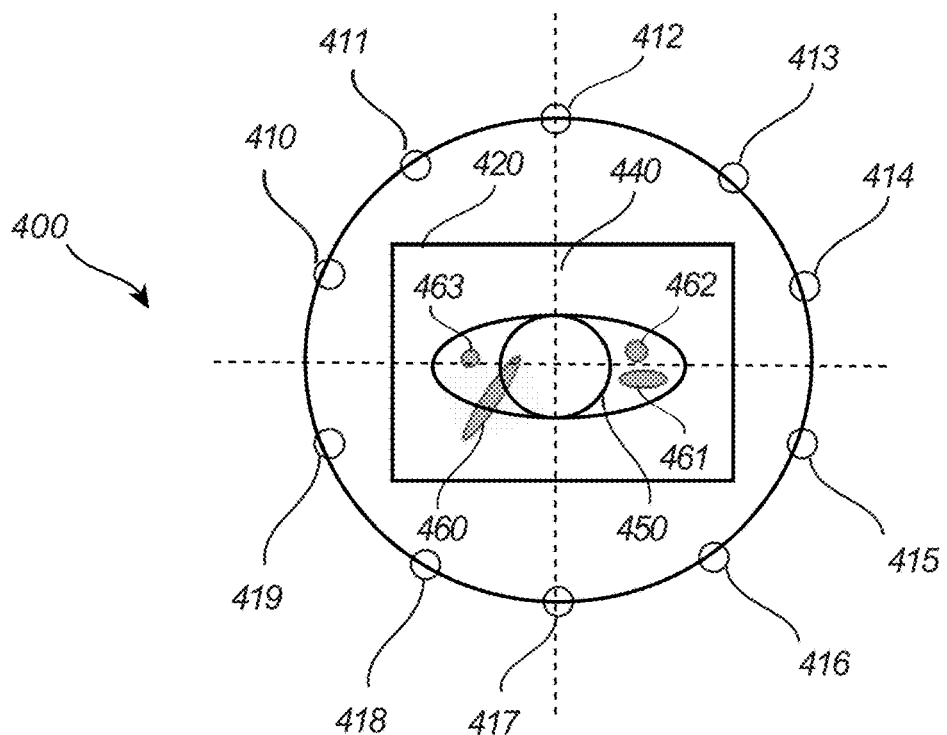
FIG. 4 shows a schematic view of an eye tracking system in relation to embodiments.

FIG. 4 shows a schematic view of an eye tracking system 400 in relation to embodiments of which examples are disclosed in the following. The eye tracking system 400 may be a head mounted system such as the system disclosed in relation to FIGS. 3a-c. The eye tracking system 400 includes a plurality of illuminators 410-419, and an image sensor 420. Each illuminator of the plurality of illuminators is located at a respective fixed position in relation to an eye of a user when the system user is using the system, i.e. when the system is mounted on the head of the user. Specifically, the plurality of illuminators 410-419 is arranged along a periphery of a circle in FIG. 4 which may for example be the periphery of one of the VR lenses of a pair of VR glasses as illustrated in FIGS. 3a-c.

For illustrative purposes, an image 440 of an eye of the user is shown on the image sensor 420.

Furthermore, it is to be noted that location of the image sensor 420 in FIG. 4 is only for illustrative purposes. The location of the sensor for one eye in a VR device is generally away from the line of sight for the user in order not to obscure a VR display arranged in the VR device for that eye. This may be achieved by means of so called hot mirrors which reflects a portion of the light and the rest of the light to pass, e.g. reflects infrared light and allows visible light to pass.

For eye tracking, the eye of the user by means of the plurality of illuminators 410-419. The image 440 is the result of the image sensor 420 detecting light from the plurality of illuminators 410-419 reflected from the eye of the user and reflected from a glass (not shown) of a pair of spectacles worn by the user. The glass of the pair of spectacles is located between the plurality of illuminators 410-419 and the eye of the user. The image 440 of the eye of the user is then received in processing circuitry (not shown) from the image sensor 420.

The processing circuitry then processes the image 440 and determines a pupil position of a representation in the image of a pupil 450 of the eye. The pupil position may be determined according to any know procedure for determining pupil position.

The processing circuitry then further identifies one or more blobs 460-463 in the image 440. A blob 460 is a representation in the image 440 of light from an illuminator of the plurality of illuminators 410-419 reflected from the glass of the pair of spectacles and detected by the image sensor 420.

As a blob (representations of reflections from an optic arrangement, such as a lens/glass of a pair of spectacles worn by the user), is generally larger in size than a glint (representation of a corneal reflection), a blob may be defined as a continuous representation of a bright spot in the image which is larger than a predefined number of pixels, where the predetermined number of pixels is preferably set such that it is larger than the number of pixel of glints and smaller than the number of pixels of blobs.

The processing circuitry then checks if there are at least one blob 460 of the one or more blobs 460-463 that meets one or more predefined criteria. On a condition that there is such a blob 460 for which the one or more predetermined criteria are met, the processing circuitry goes on to identify which illuminator of the plurality of illuminators 410-419 that is causing the blob 460 and switches off the identified illuminator.

Hence, when a new image is captured by the image sensor 420 resulting from the image sensor 420 detecting light from all illuminators of the plurality of illuminators 410-419 except the identified illuminator, the new image will not include the blob 460 for which the one or more predefined criteria are met.

In embodiments, the one or more predefined criteria comprises a predefined distance criterion and a predefined size criterion. The predefined distance criterion may for example be a criterion that the distance from the blob to the pupil position is less than a predefined distance. The predefined size criterion may for example be a criterion that the size of the blob is greater than a predefined size. In such embodiments, the processing circuitry further determines a respective position of the one or more blobs 460-463 in the image, and a respective distance from the respective position of the one or more blobs 460-463 to the pupil position. The processing circuitry further determines a respective size of the one or more blobs 460-463.

The pupil position may for example be defined as the center of the representation of the pupil 450 in the image 440. The position of a blob may be defined as the center of mass of the blob. The size of a blob may be defined as a number of pixels and may for example be calculated using Mueen's Algorithm for Similarity Search (MASS) for the blob.

The processing circuitry then checks if there is at least one blob 460 for which the predefined distance criterion is met and/or the predefined size criterion is met. On a condition that there is such a blob 460, the processing circuitry goes on to identify which illuminator of the plurality of illuminators 410-419 that is causing the at least one blob 460 of the one or more blobs 460-463 and switches off the identified illuminator.

Hence, when a new image is captured by the image sensor 420 resulting from the image sensor 420 detecting light from all illuminators of the plurality of illuminators 410-419 except the identified illuminator, the new image will not include the blob 460 for which the predefined distance criterion is met and/or the predefined size criterion is met.

In some cases, two or more blobs are identified for which the predefined distance criterion is met and/or the predefined size criterion are met, for example that these two or more blobs both have a distance to the pupil position that is less than a predefined distance according to the distance criterion and/or both blobs have a size that is greater than a predefined size according to the size criterion. For such cases, the illuminators of the plurality of illuminators 410-419 causing the two or more blobs can be identified and switched off. In alternative, a blob of the two or more blobs which is closest in distance to the pupil center of the two or more blobs can be identified and an illuminator of the plurality of illuminators 410-419 can be identified and switched off and none of the other illuminators of the plurality of illuminators 410-419 are switched off. If more than one blob of the two or more blobs are closest in distance to the pupil center, an illuminator of the plurality of illuminators 410-419 causing the blob of the more than one blobs that is largest in size is identified and switched off and none of the other illuminators of the plurality of illuminators 410-419 are switched off.

In another alternative for cases where two or more blobs are identified for which the predefined distance criterion is met and/or the predefined size criterion is met, a blob of the two or more blobs which has a largest size can be identified and an illuminator of the plurality of illuminators 410-419 can be identified and switched off and none of the other illuminators of the plurality of illuminators 410-419 are switched off. If more than one illuminator of the two or more illuminators are largest in size, an illuminator of the plurality of illuminators 410-419 causing the blob of the more than one blobs that is closest in distance to the pupil center is identified and switched off and none of the other illuminators of the plurality of illuminators 410-419 are switched off.

As a further alternative, a combination of the distance criterion and the size criterion may be used, optionally using weights between the two criteria.

In embodiments, the illuminator of the plurality of illuminators 410-419 that causes a blob 460 in a first image 440 for which the one or more predefined criteria, such as the predefined distance criterion and/or the predefined size criterion, are met can be identified by means of dividing the image into two or more regions. For example, four regions may be defined such as the four regions indicated in FIG. 4 by means of the horizontal and vertical dashed lines.

A region of the four regions in which the blob 460 for which the one or more criteria is met is identified. The blob 460 for which the one or more criteria is met is located in the lower left quarter of the image 440. A subset of illuminators associated with the identified region is then identified. For example, illuminators 417-419 arranged in a region of FIG.

4 corresponding to the region in which the blob 460 is located can be identified as the subset of illuminators. This would be based on the assumption that illuminators which in some terms are closest to the location of a blob are most likely to have caused the blob when VR lens center coincide with the image center.

Once the illuminators 417-419 of the subset of illuminators have been identified, a first illuminator 417 of the subset of illuminators is switched off. A second image of the eye is then captured by and received from the image sensor 420. The second image is the result of the image sensor 420 detecting light from the plurality of illuminators, except the first illuminator 417 being switched off, reflected from the eye of the user and reflected from the optic arrangement located between the plurality of illuminators 417-419 and the eye of the user.

It is then checked if the blob 460 for which the one or more predefined criteria were met in relation to the first image is still in the second image. If it is not, the first illuminator 417 that was switched of in relation to the second image is identified as the illuminator that caused the blob 460 for which the one or more predefined criteria were met in relation to the first image. If the blob 460 for which the one or more predefined criteria were met in relation to the first image is still in the second image, the first illuminator 417 is switched on and a second illuminator 418, is switched off. A third image of the eye is then captured by and received from the image sensor 420. The third image is the result of the image sensor 420 detecting light from the plurality of illuminators, except the second illuminator 418 being switched off, reflected from the eye of the user and reflected from the optic arrangement located between the plurality of illuminators 417-419 and the eye of the user.

It is then checked if the blob 460 for which the one or more predefined criteria were met in relation to the first image is still in the third image. If it is not, the second illuminator 418 that was switched of in relation to the third image is identified as the illuminator that caused the blob 460 for which the one or more predefined criteria were met in relation to the first image. If the blob 460 for which the one or more predefined criteria were met in relation to the first image is still in the third image, the second illuminator 418 is switched on and a third illuminator 419, is switched off. A fourth image of the eye is then captured by and received from the image sensor 420. The fourth image is the result of the image sensor 420 detecting light from the plurality of illuminators, except the third illuminator 419 being switched off, reflected from the eye of the user and reflected from the optic arrangement optic arrangement located between the plurality of illuminators 417-419 and the eye of the user.

It is then checked if the blob 460 for which the one or more predefined criteria were met in relation to the first image is still in the second image. If it is not, the third illuminator 419 that was switched of in relation to the fourth image is identified as the illuminator that caused the blob 460 for which the one or more predefined criteria were met in relation to the first image. If the blob 460 for which the one or more predefined criteria were met in relation to the first image is still in the second image, the third illuminator 419 is switched on. In this case no one of the illuminators in the subset of illuminators 417-419 associated with the region in which the blob 460 is located, it may be decided that no illuminator should be switched off or search for the illuminator causing the blob 460 is continued in other regions, preferably starting with illuminators in the region closest to the blob, which in FIG. 4 would be the upper left quarter.

Generally, after an illuminator has been switched off, it may be necessary to maintain an overall brightness of an image for glint and/or pupil detection. For example, the image needs to be bright enough for robust glint and/or pupil detection.

For example, one or more of the following may be used in order to maintain overall brightness or at least to some extent compensate for an illuminator being switched off:

Increase the luminance of other illuminators than the illuminator being switched off. This could be done by controlling the current output for one or more of the other illuminators Increase the camera aperture Increase ISO of the camera Decrease the shutter speed of the camera In summary, to maintain the brightness after switching off one or more illuminators, the luminance of one or more of the illuminators not switched off the camera's imaging parameters control to compensate for the reduced luminance due to the switching off of one or more illuminators.

Figure 5:
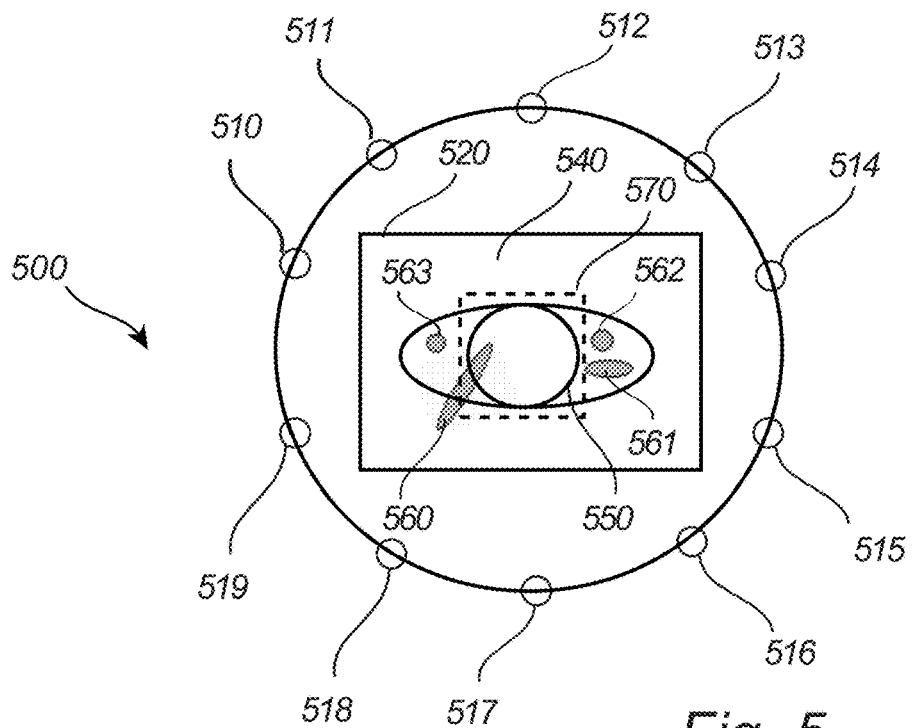
FIG. 5 shows a schematic view of an eye tracking system in relation to embodiments.

FIG. 5 shows a schematic view of an eye tracking system in relation to embodiments in which a region of interest (ROI) 570 of the image is defined.

For illustrative purposes, an image 540 of an eye of the user is shown on the image sensor 520.

Furthermore, it is to be noted that location of the image sensor 520 in FIG. 5 is only for illustrative purposes. The location of the sensor for one eye in a VR device is generally away from the line of sight for the user in order not to obscure a VR display arranged in the VR device for that eye. This may be achieved by means of so called hot mirrors which reflects a portion of the light and the rest of the light to pass, e.g. reflects infrared light and allows visible light to pass.

The region of interest 570 is a portion of the image including the representation in the image of the pupil 550. The region of interest 570 is preferably defined such that blobs 561-563 outside the region of interest 570 do not, or only in a low degree, affect the possibility to identify the representation of the pupil 550 and/or the glints in the image 540, whereas a blob 560 inside the region of interest 570 may affect the possibility to identify the representation of the pupil 550 and/or the glints in the image 540. The region of interest 570 is illustrated in FIG. 5 in dashed lines as a square but may have any other suitable shape, such as rectangle, circle, ellipse, etc. Any blobs 561-563 outside the region of interest 570 are not identified or at least not processed further. By limiting the blobs identified and further processed to any blobs 560 in the region of interest 570, the amount of processing required can be reduced. At the same time, not processing blobs 561-563 outside the region 570 of interest may not, or only to a low degree, affect the possibility to identify the representation of the pupil 550 and/or the glints in the image 540 depending on the definition of the region of interest 570.

Figure 6:
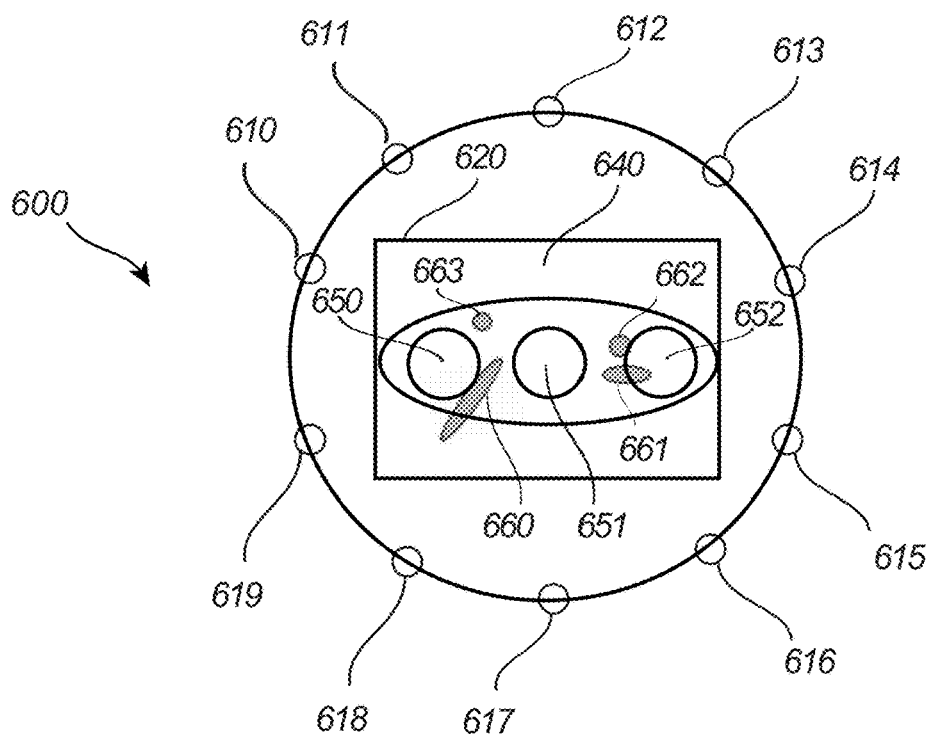
FIG. 6 shows a schematic view of an eye tracking system in relation to embodiments.

FIG. 6 shows a schematic view of an eye tracking system in relation to embodiments of which examples are disclosed in the following.

For illustrative purposes, an image 640 of an eye of the user is shown on the image sensor 620.

Furthermore, it is to be noted that location of the image sensor 620 in FIG. 6 is only for illustrative purposes. The location of the sensor for one eye in a VR device is generally away from the line of sight for the user in order not to obscure a VR display arranged in the VR device for that eye. This may be achieved by means of so called hot mirrors which reflects a portion of the light and the rest of the light to pass, e.g. reflects infrared light and allows visible light to pass.

After identifying one or more illuminators causing one or more blobs for which the one or more predefined criteria, such as the predefined distance criterion and/or the predefined size criterion, are met for a pupil position, data can be recorded in relation to different pupil positions.

In FIG. 6, images 640 for three different pupil positions 650-652 are shown superposed for illustrative purposes. The pupil is shown when it has moved to a first pupil position 650, to a second pupil position 651 and to a third pupil position 652 in the three superposed images 640.

On a condition that an illuminator is switched off for a pupil position, data that may be recorded in relation to that pupil position. If for example, a blob close to the representation of the pupil in in a first image associated with the first pupil position 650 is identified as a blob 660 for which the one or more predefined criteria, such as the predefined distance criterion and/or the predefined size criterion, are met, then an illuminator of the plurality of illuminators causing the blob 660 should be switched off for the first pupil position 650. The illuminator causing the blob 660 may for example be identified by means of one of the embodiments disclosed herein. After identification of the illuminator causing the blob 660 in the first image relating to the first pupil position 650, data can be stored in relation to the first pupil position 650.

Examples of data recorded are:
the first pupil position 650
an identification of the illuminator causing the blob 660 for which the one or more criteria are met
an association between the first pupil position 650 and the identification of the illuminator are recorded
the position of the blob 660 for which the one or more criteria are met
the size of the blob 660 for which the one or more criteria are met In embodiments where data have been recorded, the recorded data may be used for a further image captured and received after the pupil has moved from the first pupil position 650 in relation to which the data were recorded to a second pupil position 651 and then back to the first pupil position 650. In such embodiments, the eye of the user is illuminated by means of the plurality of illuminators 610-619 and a further image of the eye is received from the image sensor 620, the further image resulting from the image sensor 620 detecting light from the plurality of illuminators 610-619 reflected from the eye of the user and reflected from a glass (not shown) of a pair of spectacles located between the plurality of illuminators 610-619 and the eye of the user. A pupil position of a representation in the further image of the pupil of the eye is determined and it is determined that the pupil position in the further image is equal to the first pupil position 650. The recorded data associated with the first pupil position 650 are then used to determine which illuminator to switch off. More specifically, the recorded data include the association between the first pupil position 650 and the identification of the illuminator associated with the blob 660 for which the one or more criteria are met. Hence, the recorded data may be used to identify the illuminator to be switched off without the need for any image processing in relation to identifying blobs, position and size of blobs and distance to a pupil position in an image from each identified blob.

In embodiments where data have been recorded in relation to a first pupil position, such as the example above where a blob close to the representation of the pupil in in a first image associated with the first pupil position 650 was identified as a blob 660 for which the predefined distance criterion was met and optionally the predefined size criterion was met and data were recorded associated with the first pupil position 650. The recorded data associated with the first pupil position 650 may be used in relation to capturing a second image after the pupil has moved from the first pupil position 650 in relation to which the data were recorded to a second pupil position 651.

After the pupil has moved to the second pupil position 651, the illuminator identified by the identification as recorded in relation to the first pupil position 650 is not immediately switched on even though the second pupil position 651 is different from the first pupil position 650. Instead, the eye of the user is illuminated by means of the plurality of illuminators 610-619, except the illuminator as identified by the identification as recorded associated with the first pupil position 650. A second image of the eye is captured by and received from the image sensor 620, the second image resulting from the image sensor detecting light from the plurality of illuminators 610-619, except the illuminator as identified by the identification as recorded for the first pupil position 650, reflected from the eye of the user and reflected from the optic arrangement located between the plurality of illuminators 610-619 and the eye of the user.

The second pupil position 651 of the representation in the second image of the pupil of the eye is determined, and since the pupil has moved, it is determined that the second pupil position 651 is different from the first pupil position 650 as recorded.

The recorded data are used in determining a further distance from the position of the blob 660 as recorded associated with the first pupil position 650, i.e. the blob 660 for which the predefined distance criterion was met and optionally the predefined size criterion was met in relation to the first pupil position 650, to the second pupil position 651. On a condition that the determined further distance meets the predefined distance criterion, the illuminator identified by the identification as recorded in relation to the first pupil position is maintained switched off. On a condition that the determined further distance does not meet the predefined distance criterion, the illuminator identified by the identification as recorded in relation to the first pupil position is switched on.

In embodiments where data are recorded, the recording may be performed continuously for each new pupil position, e.g. for the first pupil position 650, the second pupil position 651 and the third pupil position 652, for which no data have been previously recorded. For pupil positions for which data have been recorded, the recorded data may for example be used to switch off an illuminator identified by the recorded data, i.e. removal of a blob in the image may be done instantly as soon as a particular pupil position has been determined.

Figure 7:
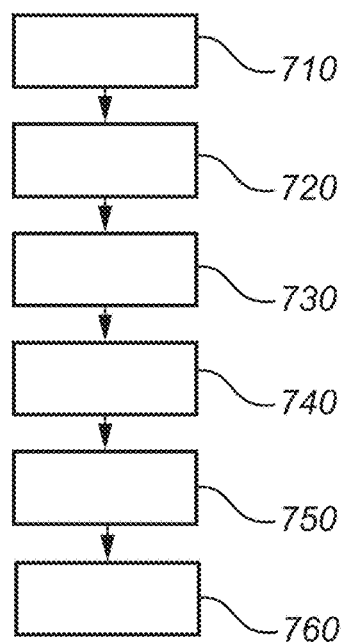

FIG. 7 shows a method according to an embodiment of controlling illuminators in an eye tracking system, wherein the system includes a plurality of illuminators arranged such that each illuminator of the illuminators is located at a respective fixed position in relation to an eye of a user when using the system. The method comprises illuminating 710 the eye of the user by means of the plurality of illuminators. The method further comprises receiving 720 an image of the eye of the user from an image sensor, the image resulting from the image sensor detecting light from the plurality of illuminators reflected from the eye of the user and reflected from an optic arrangement located between the plurality of illuminators and the eye of the user. The method further comprises determining 730 a pupil position of a representation in the image of a pupil of the eye, and identifying 740 one or more blobs in the image, wherein a blob is a representation in the image of a reflection from the optic arrangement of light from an illuminator of the plurality of illuminators. On a condition that there is at least one blob of the one or more blobs for which one or more predefined criteria are met, the method further comprises identifying 750 an illuminator of the plurality of illuminators associated with the at least one blob of the one or more blobs and switching off 760 the identified illuminator of the plurality of illuminators.

FIG. 8 shows a method according to another embodiment of controlling illuminators in an eye tracking system, wherein the system includes a plurality of illuminators arranged such that each illuminator of the illuminators is located at a respective fixed position in relation to an eye of a user when using the system. The method according to an embodiment. The method comprises illuminating 810 the eye of the user by means of the plurality of illuminators. The method further comprises receiving 820 an image of the eye of the user from an image sensor, the image resulting from the image sensor detecting light from the plurality of illuminators reflected from the eye of the user and reflected from an optic arrangement located between the plurality of illuminators and the eye of the user. The method further comprises determining 830 a pupil position of a representation in the image of a pupil of the eye, and identifying 840 one or more blobs in the image, wherein a blob is a representation in the image of a reflection from the optic arrangement of light from an illuminator of the plurality of illuminators. The method further comprises determining 850 a respective position of the one or more blobs in the image, determining 860 a respective distance from the respective position of the one or more blob to the pupil position, and determining 870 a respective size of the one or more blobs. On a condition that there is at least one blob of the one or more blobs for which the determined distance of the at least one blob of the one or more blobs meets a predefined distance criterion and/or the determined size of the at least one blob of the one or more blobs meets a predefined size criterion, the method further comprises identifying 880 an illuminator of the plurality of illuminators associated with the at least one blob of the one or more blobs and switching off 890 the identified illuminator of the plurality of illuminators.

FIG. 9 shows a method in relation to embodiments in which identification of an illuminator of a plurality of illuminator is causing a blob for which one or more criteria are met. The method comprises dividing 910 the image into two or more regions, identifying 920 a region of the two or more regions in which the blob for which the one or more criteria are met is located, and identifying 930 a subset of illuminators of the plurality of illuminators, the subset of illuminator being associated with the identified region. The method further comprises switching off 940 an illuminator of the identified subset of illuminators, receiving 950 a further image of the eye from the image sensor, the further image resulting from the image sensor detecting light from the plurality of illuminators, except the illuminator being switched off, reflected from the eye of the user and reflected from the optic arrangement located between the plurality of illuminators and the eye of the user. On a condition 970 that the at least one blob of the one or more blobs is in the further image switching on 980 the illuminator that was switched of in relation to the further image, and repeating, for a different illuminator of the subset of illuminators, the steps of switching off 940 an illuminator and receiving 950 a further image. On a condition 970 that the at least one blob of the one or more blobs is not in the further image, identifying 990 the illuminator being switched off in relation to the further image as the illuminator causing the blob for which one or more criteria are met.

Figure 10:
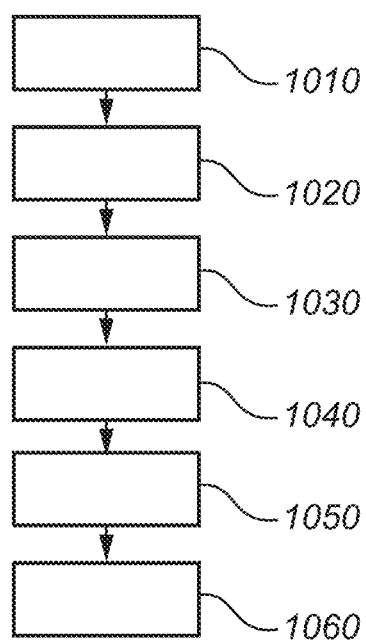

FIG. 10 shows a method in relation to embodiments in which data are recorded for a pupil position in relation to a blob for which one or more predefined criteria are met and an illuminator causing the blob is switched off.

The method comprises recording 1010:
the pupil position
an identification of the illuminator of the plurality illuminators associated with the blob for which the one or more criteria are met
an association between the pupil position and the identification of the illuminator
the position of the blob for which the one or more criteria are met
the size of the blob for which the one or more criteria are met The method further comprises illuminating 1020 the eye of the user by means of the plurality of illuminators, and receiving 1030 a further image of the eye from the image sensor, the further image resulting from the image sensor detecting light from the plurality of illuminators reflected from the eye of the user and reflected from the spectacle glass located between the plurality of illuminators and the eye of the user. The method further comprises determining 1040 a further pupil position of a representation in further the image of a pupil of the eye, determining 1050 that the further pupil position is equal to the pupil position as recorded, and switching off 1060 the illuminator as identified by the identification as recorded and association to the pupil position as recorded.

Figure 11:
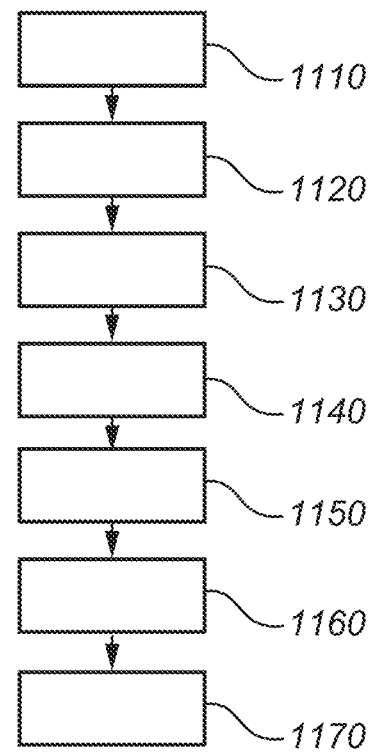

FIG. 11 shows a method in relation to embodiments in which data are recorded for a pupil position in relation to a blob for which a predefined distance criterion is met and/or a predefined size criterion is met and an illuminator causing the blob is switched off.

The method comprises recording 1110:
the pupil position
an identification of the illuminator of the plurality illuminators associated with the blob for which the predefined distance criterion is met and/or the predefined size criterion is met
an association between the pupil position and the identification of the illuminator
the position of the blob for which the predefined distance criterion is met and/or the predefined size criterion is met
the size of the blob for which the predefined distance criterion and/or the predefined size criterion are met The method further comprises illuminating 1120 the eye of the user by means of the plurality of illuminators, except the illuminator as identified by the identification as recorded, and receiving 1130 a further image of the eye from the image sensor, the further image resulting from the image sensor detecting light from the plurality of illuminators, except the illuminator as identified by the identification as recorded, reflected from the eye of the user and reflected from the optic arrangement located between the plurality of illuminators and the eye of the user. The method further comprises determining 1140 a further pupil position of a representation in further the image of a pupil of the eye, determining 1150 that the further pupil position is different from the pupil position as recorded, and determining 1160 a further distance from the position of the at least one blob as recorded to the further pupil position. On a condition that the determined further distance meets the predefined distance criterion the method comprises maintaining 1170 the illuminator identified by the identification as recorded switched off.

A person skilled in the art realizes that the present invention is by no means limited to the preferred embodiments described above. On the contrary, many modifications and variations are possible within the scope of the appended claims. For example, the person skilled in the art realizes that the methods described herein may be performed by other eye/gaze tracking systems than the example eye/gaze tracking system 100 shown in FIG. 1, for example any eye/gaze tracking system in which the location of illuminators is fixed in relation to the eyes of a user when the system is used. Furthermore, the embodiments in relation to FIGS. 4-9 have been described for one eye. However, a person skilled in the art realizes that the methods may be performed for two eyes also where the result for both eyes is taken into account in each step.

Additionally, variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The division of tasks between functional units referred to in the present disclosure does not necessarily correspond to the division into physical units; to the contrary, one physical component may have multiple functionalities, and one task may be carried out in a distributed fashion, by several physical components in cooperation. A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems. The mere fact that certain measures/features are recited in mutually different dependent claims does not indicate that a combination of these measures/features cannot be used to advantage. Method steps need not necessarily be performed in the order in which they appear in the claims or in the embodiments described herein, unless it is explicitly described that a certain order is required. Any reference signs in the claims should not be construed as limiting the scope.

The invention claimed is:

1. A method of controlling illuminators in an eye tracking system, the method comprising:
    illuminating an eye of a user via a plurality of illuminators, wherein the plurality of illuminators are arranged such that each illuminator of the illuminators is located at a respective fixed position in relation to the eye of the user when using the eye tracking system;
    receiving an image of the eye of the user from an image sensor, the image resulting from the image sensor detecting light from the plurality of illuminators reflected from the eye of the user and reflected from an optic arrangement located between the plurality of illuminators and the eye of the user;
    determining a pupil position of a representation in the image of a pupil of the eye;
    identifying one or more blobs in the image, wherein a blob is a representation in the image of a reflection from the optic arrangement of light from an illuminator of the plurality of illuminators; and
    on a condition that there is at least one blob of the one or more blobs for which one or more predefined criteria are met:
    identifying an illuminator of the plurality of illuminators associated with the at least one blob of the one or more blobs; and
    switching off the identified illuminator of the plurality illuminators.

2. The method of claim 1, further comprising:
    determining a respective position of the one or more blobs in the image;
    determining a respective distance from the respective position of the one or more blob to the pupil position; and
    determining a respective size of the one or more blobs, wherein the one or more predefined criteria comprises a predefined distance criterion and/or a predefined size criterion and wherein on a condition that the determined distance of at least one blob of the one or more blobs meets a predefined distance criterion and/or the determined size of the at least one blob of the one or more blobs meets a predefined size criterion:
    identifying an illuminator of the plurality of illuminators associated with the at least one blob of the one or more blobs; and
    switching off the identified illuminator of the plurality illuminators.

3. The method of claim 2, wherein the pupil position is determined as the position of the center of the representation of the pupil in the image and the position of a blob is determined as the position of the center of mass of the blob.

4. The method of claim 3, wherein the distance criterion is met on a condition that the determined distance is below a predefined distance.

5. The method of claim 3, wherein the size criterion is met on a condition that the determined size is above a predefined size.

6. The method of claim 2, further comprising:
    recording, on a condition that an illuminator is switched off, the pupil position, an identification of the illuminator of the plurality illuminators associated with the at least one blob of the one or more blobs, an association between the pupil position and the identification of the illuminator, the position of the at least one blob of the one or more blobs, the size of the at least one blob of the one or more blobs.

7. The method of claim 6, further comprising:
on a condition that an illuminator is switched off:
    illuminating the eye of the user by means of the plurality of illuminators, except the illuminator as identified by the identification as recorded;
    receiving a further image of the eye from the image sensor, the further image resulting from the image sensor detecting light from the plurality of illuminators, except the illuminator as identified by the identification as recorded, reflected from the eye of the user and reflected from the optic arrangement located between the plurality of illuminators and the eye of the user;
    determining a further pupil position of a representation in further the image of a pupil of the eye;
    determining that the further pupil position is different from the pupil position as recorded;
    determining a further distance from the position of the at least one blob as recorded to the further pupil position; and on a condition that the determined further distance meets the predefined distance criterion maintaining the illuminator identified by the identification as recorded switched off.

8. The method of claim 1, wherein identifying an illuminator of the plurality of illuminators comprises:
dividing the image into two or more regions,
identifying a region of the two or more regions in which the at least one blob of the one or more blobs is located;
identifying a subset of illuminators of the plurality of illuminators, the subset of illuminator being associated with the identified region;
switching off an illuminator of the identified subset of illuminators;
receiving a further image of the eye from the image sensor, the further image resulting from the image sensor detecting light from the plurality of illuminators, except the illuminator being switched off, reflected from the eye of the user and reflected from the optic arrangement located between the plurality of illuminators and the eye of the user;
on a condition that the at least one blob of the one or more blobs is in the further image, repeating, for a different illuminator of the subset of illuminators, the steps of switching off an illuminator and receiving a further image until the at least one blob of the one or more blobs is not in the further image.

9. The method of claim 1, wherein the one or more blobs are further identified in a region of interest of the image, the region of interest being a portion of the image including the representation in the image of the pupil.

10. The method of claim 1, further comprising:
on a condition that an illuminator is switched off, recording:
the pupil position,
an identification of the illuminator of the plurality illuminators associated with the at least one blob of the one or more blobs, and
an association between the pupil position and the identification of the illuminator.

11. The method of claim 10, further comprising:
illuminating the eye of the user using the plurality of illuminators;
receiving a further image of the eye from the image sensor, the further image resulting from the image sensor detecting light from the plurality of illuminators reflected from the eye of the user and reflected from the spectacle glass located between the plurality of illuminators and the eye of the user;
determining a further pupil position of a representation in further the image of a pupil of the eye;
determining that the further pupil position is equal to the pupil position as recorded; and
switching off the illuminator as identified by the identification as recorded and association to the pupil position as recorded.

12. The method of claim 1, wherein a blob is a representation of a reflection in the image having a size larger than a blob threshold size.

13. An eye tracking system comprising:
a plurality of illuminators configured to illuminate an eye of a user, the plurality of illuminators being arranged at fixed positions in relation to an eye of a user when using the device;
a receiver configured to receive an image of the eye of the user from an image sensor, the image resulting from the image sensor detecting light from the plurality of illuminators reflected from the eye of the user and reflected from an optic arrangement located between the plurality of illuminators and the eye of the user;
processing circuitry configured to:
determine a pupil position of a representation in the image of a pupil of the eye, identifying one or more blob in the image, wherein a blob is a representation in the image of a reflection from the optic arrangement of light from an illuminator of the plurality of illuminators; and
on a condition that at least one blob of the one or more blobs meets one or more predefined criteria:
identify an illuminator of the plurality of illuminators associated with the at least one blob of the one or more blobs; and
switch off the identified illuminator of the plurality illuminators.

14. The system of claim 13, wherein the one or more predefined criteria comprises a predefined distance criterion and a predefined size criterion, and wherein the processing circuitry is further configured to:
determine a respective position of the one or more blobs in the image;
determine a respective distance from the respective position of the one or more blob to the pupil position;
determine a respective size of the one or more blobs; and
on a condition that the determined distance of at least one blob of the one or more blobs meets a predefined distance criterion and/or the determined size of the at least one blob of the one or more blobs meets a predefined size criterion:
identify an illuminator of the plurality of illuminators associated with the at least one blob of the one or more blobs; and
switch off the identified illuminator of the plurality illuminators.

15. A eye tracking system comprising circuitry configured to implement a method comprising:
illuminating an eye of a user via a plurality of illuminators, wherein the plurality of illuminators are arranged such that each illuminator of the illuminators is located at a respective fixed position in relation to the eye of the user when using the eye tracking system;
receiving an image of the eye of the user from an image sensor, the image resulting from the image sensor detecting light from the plurality of illuminators reflected from the eye of the user and reflected from an optic arrangement located between the plurality of illuminators and the eye of the user;
determining a pupil position of a representation in the image of a pupil of the eye;
identifying one or more blobs in the image, wherein a blob is a representation in the image of a reflection from the optic arrangement of light from an illuminator of the plurality of illuminators; and
on a condition that there is at least one blob of the one or more blobs for which one or more predefined criteria are met:
identifying an illuminator of the plurality of illuminators associated with the at least one blob of the one or more blobs; and
switching off the identified illuminator of the plurality illuminators.

16. The eye tracking system of claim 15, the method further comprising:
determining a respective position of the one or more blobs in the image;

determining a respective distance from the respective position of the one or more blob to the pupil position; and determining a respective size of the one or more blobs, wherein the one or more predefined criteria comprises a predefined distance criterion and/or a predefined size criterion and wherein on a condition that the determined distance of at least one blob of the one or more blobs meets a predefined distance criterion and/or the determined size of the at least one blob of the one or more blobs meets a predefined size criterion:

identifying an illuminator of the plurality of illuminators associated with the at least one blob of the one or more blobs; and switching off the identified illuminator of the plurality illuminators.

17. The eye tracking system of claim 16, wherein the pupil position is determined as the position of the center of the representation of the pupil in the image and the position of a blob is determined as the position of the center of mass of the blob.

18. One or more computer-readable storage media storing computer-executable instructions that, when executed by a processor, cause the processor to perform a method comprising:

illuminating an eye of a user via a plurality of illuminators, wherein the plurality of illuminators are arranged such that each illuminator of the illuminators is located at a respective fixed position in relation to the eye of the user when using the eye tracking system;

receiving an image of the eye of the user from an image sensor, the image resulting from the image sensor detecting light from the plurality of illuminators reflected from the eye of the user and reflected from an optic arrangement located between the plurality of illuminators and the eye of the user;

determining a pupil position of a representation in the image of a pupil of the eye;

identifying one or more blobs in the image, wherein a blob is a representation in the image of a reflection from the optic arrangement of light from an illuminator of the plurality of illuminators; and on a condition that there is at least one blob of the one or more blobs for which one or more predefined criteria are met:

identifying an illuminator of the plurality of illuminators associated with the at least one blob of the one or more blobs; and switching off the identified illuminator of the plurality illuminators.

\* \* \* \* \*